United States Patent [19]
Vance et al.

[11] Patent Number: 5,358,485
[45] Date of Patent: Oct. 25, 1994

[54] CUTTER FOR ATHERECTOMY CATHETER

[75] Inventors: Jeffrey D. Vance, Hugo; Rick L. Shockey, Coon Rapids, both of Minn.

[73] Assignee: Schneider (USA) Inc., Plymouth, Minn.

[21] Appl. No.: 109,003

[22] Filed: Aug. 16, 1993

Related U.S. Application Data

[63] Continuation of Ser. No. 819,780, Jan. 13, 1992, abandoned.

[51] Int. Cl.$^5$ ............................................. A61B 17/22
[52] U.S. Cl. ...................................... 604/22; 606/159
[58] Field of Search ................ 606/159, 170, 180; 604/22

[56] References Cited

U.S. PATENT DOCUMENTS

| | | |
|---|---|---|
| 4,207,874 | 6/1980 | Choy . |
| 4,445,509 | 5/1984 | Auth . |
| 4,748,979 | 6/1988 | Hershenson . |
| 4,784,636 | 11/1988 | Rydell . |
| 4,857,045 | 8/1989 | Rydell . |
| 4,895,166 | 1/1990 | Farr et al. .................. 128/751 |
| 4,957,482 | 9/1990 | Shiber ......................... 604/22 |
| 5,030,201 | 7/1991 | Palestrant .................. 604/22 |
| 5,084,010 | 1/1992 | Plaia et al. .............. 606/159 X |
| 5,100,425 | 3/1992 | Fischell et al. ............. 606/159 |
| 5,114,399 | 5/1992 | Kovalcheck ................. 604/22 |
| 5,154,724 | 10/1992 | Andrews ..................... 606/159 |

FOREIGN PATENT DOCUMENTS

0427367  5/1991  European Pat. Off. .
90/02523  3/1990  PCT Int'l Appl. .

*Primary Examiner*—Michael H. Thaler
*Attorney, Agent, or Firm*—Haugen and Nikolai

[57] ABSTRACT

An atherectomy catheter is provided with an improved high speed rotating cutting head is disclosed in which the cutting head has a generally oval-shaped nose portion which includes a plurality of radially disposed excising openings extending along and rearward from a point near the center of the nose. The openings are elongated but do not extend beyond the elliptical portion of reduced diameter, and, therefore, do not damage the lining of the vessel involved.

12 Claims, 2 Drawing Sheets

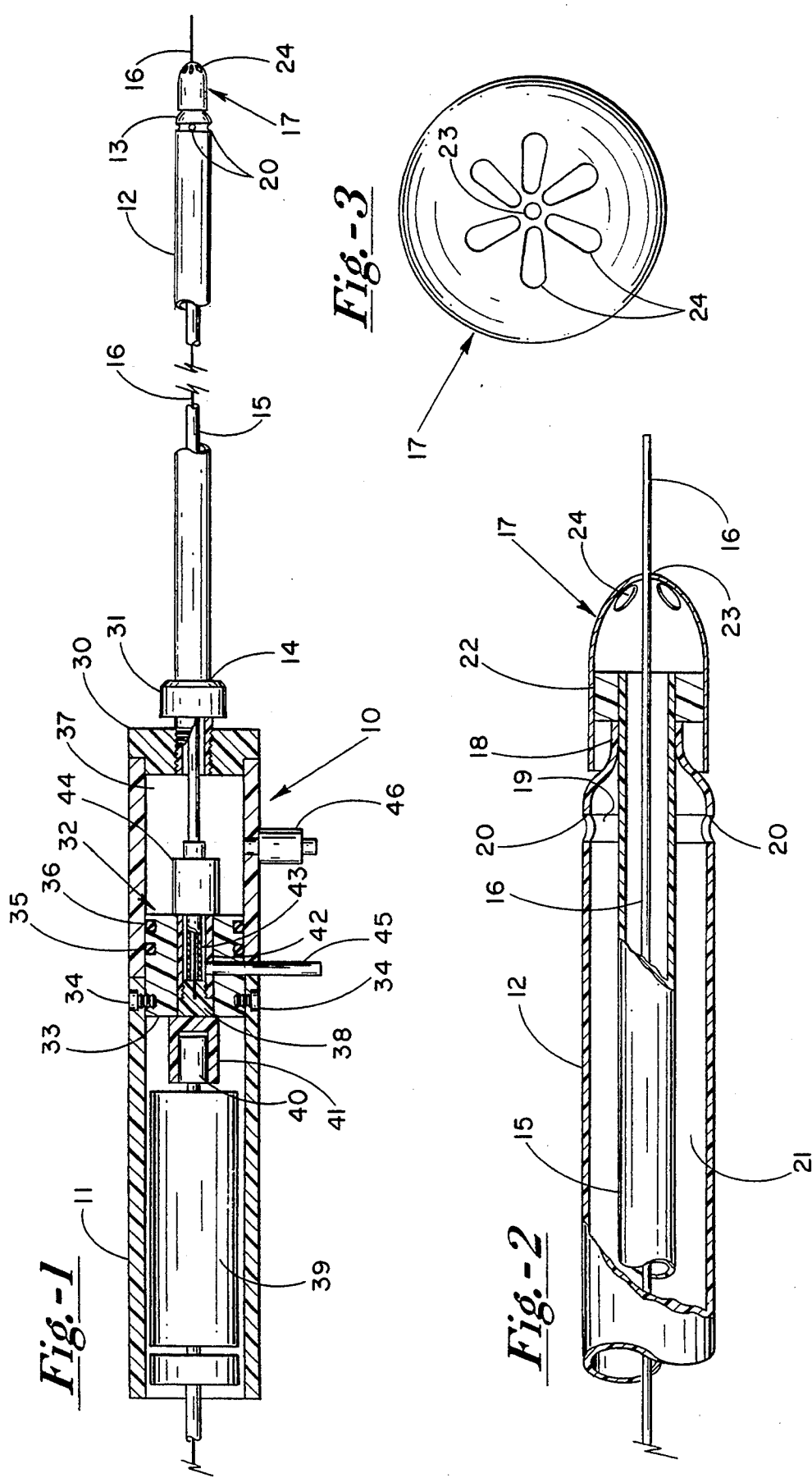

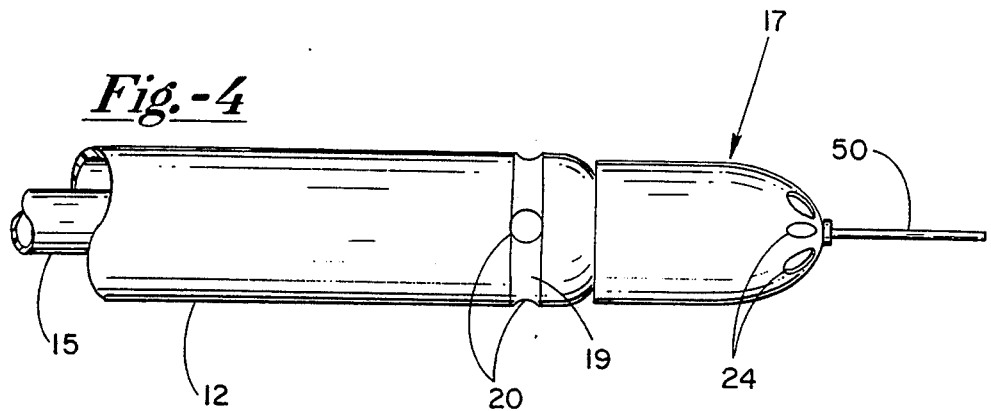
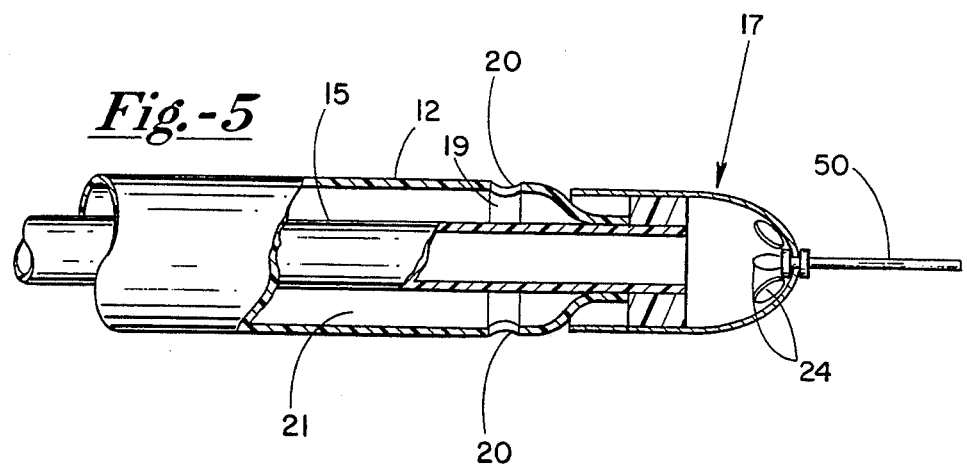
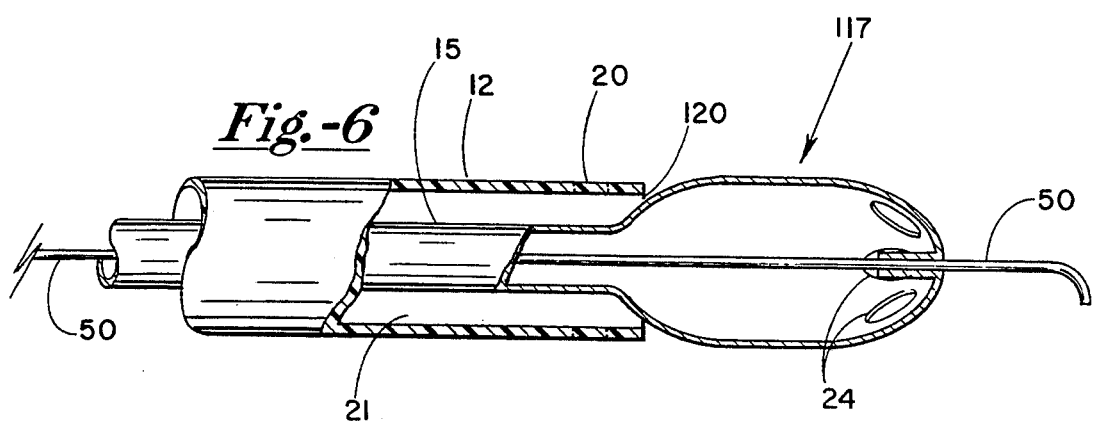

CUTTER FOR ATHERECTOMY CATHETER

This is a continuation of copending application Ser. No. 07/819,780, filed on Jan. 13, 1992, now abandoned.

BACKGROUND OF THE INVENTION

1. Field of the Invention

The present invention relates to a relatively non-invasive plaque resolving device of the class adapted to be inserted through the lumen of a blood vessel and manipulated therethrough to a desired location to ply a cutting tool to excise deposits of atherosclerotic plaque from the internal surfaces of the vessel. More particularly, the present invention relates to an improved cutting tool for use in such a system.

2. Related Art

Impairment of the circulation of blood occasioned by intraarterial deposits of atherosclerotic plaque is a major symptom of cardiovascular disease. Obstruction of coronary arteries can lead to tissue death because of oxygen deprivation of heart muscle. Coronary infarction (heart attack) is the result. Plaque-induced stenosis of other major arteries can result in impairment of peripheral organ function. One long-used procedure for overcoming such obstructions and blockages involves a surgical by-pass operation in which the obstructed arteries are subtended by patient autographed blood vessels removed from other parts of the patient's body. Surgically invasive endarterectomy has also been used with limited success for clearing obstructed vessels.

The need has long existed for a less invasive and radical procedure to alleviate such blockages and achieve transmyocardial revascularization, or the like, in a manner which causes no significant damage to the healthy endothelial lining of the surrounding vessel. One technique that attempts to fulfill this need is balloon angioplasty in which an inflatable balloon is passed to the stenotic region of the affected artery and inflated with a fluid to a pressure (normally, about 5 atmospheres) to depress the plaque against the arterial wall thereby opening up the arterial volume. Because circulation is grossly impaired, however, balloon inflation/deflation must occur in a matter of seconds to avoid infarction. In addition, limited force is available because of the fear of damage to the arteries caused by overpressurization of the balloon. Also, the capture of plaque debris that may slough during the expansion process is not as yet provided for by such devices.

Other approaches include the use of a laser to clear obstructions in vessels as proposed, for example, in U.S. Pat. No. 4,207,874 to Choy. In that device, laser energy is conveyed by flexible fiberoptics in conjunction with a vascular catheter and applied to the plaque obstruction in the occluded zone. In conjunction with this system various axial channels may be provided with appropriate fluid management manifolds in order to inject saline, aspirate debris with the saline and inject dye for visualization. Additional coherently aligned fibers may be provided for actual viewing of the obstruction intraluminally. In addition to Choy, many other approaches utilizing variations on a laser excising system have also been proposed. Lasers, for example, have been utilized to resolve plaque by heating a catheter tip in a manner which causes the plaque tissue to, in effect, be melted away by the heated tip of the catheter resulting in permanent removal. That approach is illustrated by Hershenson in U.S. Pat. No. 4,748,979.

A variety of cutting devices have also been proposed in conjunction with catheters in which rotating cutters actually address and excise the stenosis. Presently known devices, however, have not been able to combine the required ability to achieve rapid cutting of the stenosis with the equally important ability to do so without a high degree of risk of affecting or damaging the relatively soft adjacent wall of the arterial vessel involved.

One such device is disclosed in U.S. Pat. No. 4,784,636 to Rydell which is assigned to the same assignee as the present invention. That invention provides an atherectomy catheter which includes a guide catheter having an inflatable balloon disposed on the distal end portion thereof, the guide catheter being dimensioned to receive an elongated drive tube having an angular cutting tip affixed to the distal end thereof. A rotational drive mechanism is coupled to the drive tube at its proximal end for rotating the cutting tip. Provision is also made in the drive mechanism for introducing fluid through the lumen of the guide catheter for inflating the balloon and for drawing a vacuum on the lumen of the drive tube for aspirating the treatment site. In use, the guide catheter with the drive tube and cutter head retracted is advanced up to the occlusion and then, the balloon is inflated to lock the distal end in place. Next the cutter is rotated at high speed and advanced into the occlusion, while blood and any loose particular matter is aspirated. The balloon is then deflated and advanced further into the lesion and the steps repeated until the occlusion is removed.

A more recently issued patent to Rydell, also of common assignee with the prior above-referenced patent, is U.S. Pat. No. 4,857,045 which is directed to a self-guiding atherectomy catheter system utilizing coaxial inner and outer flexible tubular members in which the inner tubular member is journaled for rotation at the distal end of the outer tubular member. A motor located at the proximal end of the catheter assembly drives the inner tubular member including a cutter head fixed to the inner tubular member at a point just beyond the end portion of the outer tubular member. Aspiration is accomplished through the inner tubular member and a flushing fluid such as saline administered through the outer tubular member, as required.

That reference further discloses a dome-shaped rotational cutting head containing a large number of substantially round open ports for addressing blockage material upon rotation. When the cutting head is rotated, the open ports directly address the plaque but are not precluded from cutting into the arterial lining and wall if extreme care is not taken with respect to the use of the device.

While the last-discussed system represents an improvement with regard to centering and operating the atherectomy catheter within a vessel of interest, there remains a need to improve the safety of cutting devices of the class described with respect to reducing and preventing damage to the vessel of interest including its inner lining which may be occasioned when removing a stenosis. There also exists a need to improve the ability of the operator to guide the catheter in navigating the vascular system to reach the situs of the occlusion of interest. Guidewires have been used with success in several types of catheters but heretofore have not been used with rotating atherectomy devices because of the need to coordinate the guidewire placement to avoid the cutter head.

SUMMARY OF THE INVENTION

The present invention provides an improved cutting head member or cutting tool for use on an atherectomy catheter device. The tool is secured to the distal tip portion of the inner tubular member of an atherectomy catheter of the coaxial type having large and small concentrically disposed elongated flexible tubular members in one preferred embodiment. The cutting member of the invention itself is a substantially hollow peripherally symmetrical body having a generally oval-shaped distal nose portion containing a plurality of openings extending along and rearward from the nose. The openings are in communication with the hollow interior and radially disposed about the tip. The edge of each opening contacting adjacent tissue operates to excise the tissue upon rotation of the cutting tool. The excised tissue is directed through the opening into the hollow interior of the cutting tool.

With respect to the cutting tool shape, any symmetrical oval, ogine or dome shape which accomplishes the desired diameter reduction in the vicinity of the cutting openings can be used. In this manner, the tool may be in the form of a circular cylinder having a generally oval- or elliptical-shaped nose, or in the shape of a fully oval member; an ellipse represents but one acceptable shape.

The concentrically disposed, elongated flexible tubular members have a respective inside and outside measurement allowing sufficient clearance between the two whereby fluid may be passed through the lumen of the outer tubular member and out through the end of the lumen and/or one or more ports formed through the wall of the outer tubular member near its distal end. The inner tubular member is secured to a drive means at is proximal end which is configured to rotate the inner tubular member relative to the outer tubular member. The system also allows the simultaneous infusion of a liquid through the outer tubular member and the aspiration of fluids and debris through the lumen of the inner tubular member. In this manner, the site of the lesion to be excised or any desired location can be flooded with a flushing liquid as desired. When the operating cutter is advanced into the lesion, the flushing fluid, and the debris sectioned from the lesion, are directed into the hollow cutting head and are aspirated into the lumen of the inner tubular member, which is connected with the hollow interior of the cutter head, and are collected in a suitable vessel connected to an outlet at the proximal end of the assembly.

The system is further provided with a guidewire to enable easier guiding of the catheter through the vascular system to the site of the lesion. In one embodiment the guidewire extends through the inner tubular member and drive shaft and is fixed beyond the proximal end thereof such that it is permitted to remain stationary while the catheter is able to move freely along it. In the alternative embodiment, a short guidewire is mounted to and journalled in a central opening in the nose of the cutting tool head in a manner which provides a clearance which allows it to rotate with the member if the end of the guidewire is free to do so or remain stationary if resistance to rotation of the guidewire occurs. In either embodiment the guidewire is adapted to extend through a central hole in the nose of the cutting tool in a manner which does not interfere with the operation of the rotating cutter.

The openings in the rotating cutter member are located in the narrowed front portion of the oval-shaped nose in a manner which precludes contact between the cutter openings and the sides or walls of the vessel of interest during operation as normally positioned. This minimizes the possibility of damage occurring to the lining of the vessel or to the vessel wall during operation of the cutting tool. The cutting tool is adapted to be driven at relatively high speed, so that the material such as fatty tissue excised is extremely finely divided prior to its being aspirated back through the lumen of the inner catheter. Speeds up to 30,000 rpm are achieved.

BRIEF DESCRIPTION OF THE DRAWINGS

In the drawings:

FIG. 1 is a view, partially in section, broken, with parts cut away, illustrating an atherectomy catheter employing one embodiment of the present invention;

FIG. 2 is a greatly enlarged fragmentary view, with parts cut away, showing one cutter head arrangement;

FIG. 3 is an end view of the cutter head of FIG. 2 still further enlarged;

FIG. 4 is a view illustrating an alternative embodiment of the cutter head of FIG. 2;

FIG. 5 is a partial sectional view of the embodiment of FIG. 4; and

FIG. 6 is a view similar to FIG. 5 of another alternate embodiment.

DESCRIPTION OF THE PREFERRED EMBODIMENTS

The present invention involves an atherectomy catheter in which a rotatable cutter is disposed at the distal end and in which means are provided at the proximal end for driving the cutter at a high rotational speed while simultaneously injecting a flushing liquid and aspirating the treatment site. The invention further provides a cutter head or cutter tool of improved safety coordinated and operated with a guidewire system to aid and facilitate guiding the catheter through the tortuous path of the vascular system to the treatment site. The invention will be described with particular reference to the drawing figures in which like numerals will be utilized to designate like parts throughout the same.

FIG. 1 illustrates the surgical device of the present invention with respect to a typical atherectomy catheter system which is indicated generally by the numeral 10. The system includes a control and drive system located within a proximal housing 11, which may be of high impact plastic material. The catheter itself is of the coaxial bi-lumener type. The housing is connected to an elongated outer flexible tubular member 12 extending between a distal end 13 and a proximal end 14 fixed to the housing 11. The hollow lumen of the outer tubular member 12 carries a concentrically disposed, coaxial elongated, flexible inner tubular member 15 which extends beyond the full length of the outer tubular member 12. The inner tubular member 15, in the embodiment of FIG. 1, also is threaded over a non-rotating or stationary guidewire 16 which extends the full length of the inner tubular member 15 and protrudes therefrom and along which the catheter is free to travel.

As can better been seen in FIGS. 2 and 3, and will be described in greater detail below, the distal end of the catheter carries a hollow cutting head or cutting tool 17 which is fixed to the inner tubular member 15 and is free to rotate about the outer tubular member 12. The outer tubular member 12 is tapered down to a distal end portion 18 that creates a bearing surface which allows easy journaled rotation of the inner tube 15 carrying cutter head 17. An infusion system is provided including an indented annular area of reduced diameter 19 near the distal end of the outer tubular member 12 which contains a series of radially disposed openings or holes 20 (FIG. 1). Liquid contained in the annular space in the lumen of the member 12 surrounding the member 15 as at 21 can be ejected through the holes 20 to flush the operating site. An annular spacer member 22 is provided which is bonded both to the distal tip of the inner tubular member 15 and the inner surface of the cutter head 17 to fix the cutter head to the distal tip of the inner tubular member 15.

The guidewire 16 is slidably threaded and extends through a central hole 23 in the distal tip of the cutter member 17, throughout the length of the inner tubular member 15 and housing, and is separately controlled. The catheter system is free to move along the guidewire, and it is designed to remain stationary as the cutter head member 17 is rotated. The cutter head 17 contains a plurality of elongated openings 24 disposed in radial symmetry about the center of the distal nose as shown in FIG. 3. The cutter head may typically be initially cylindrical and taper off in a symmetrical oval shape as it approaches the distal end. The plurality of openings 24 is usually an even number from two to six and the openings are placed close to the nose of the oval-shaped cutter head 17 so that the possibility of inadvertently contacting and cutting the side wall of the vessel parallel to the member 22 from which the plaque or other blockage is to be excised is virtually eliminated.

A drive means is contained within the rigid tubular housing 11 located at the proximal end of the outer tubular member. The drive functions to rotate the inner tubular member within the lumen of the outer tubular member. The outer tubular member is joined to the tubular housing 11 as through end plug member 30 and is secured as by a compression fitting 31 which creates a liquid-tight seal. A rotary union shown generally at 32 is positioned within the housing 11 and includes a stationary tubular sleeve member 33 fixed to the housing 11 by pins or screws 34. A pair of O-ring seals 35 and 36 are disposed in annular grooves in the tubular sleeve 33 to preclude flushing liquid contained in the chamber 37 from passing beyond the rotary union.

Inside of the stationary sleeve 33 is a rotating hollow manifold member 38 which rotates within the bore of the member 33 when driven by a motor such as that depicted generally at 39 having a drive shaft 40 and a coupling 41 connected in driving relation to the proximal end of the hollow manifold member 38. The hollow manifold member 38 further contains an annular recess 42 connected to a central bore 43 which, in turn, is joined to the proximal end of the inner elongated flexible tubular member 15 by a coupling member 44. The central inner bore 43, via the annular recess 42, is connected to a further tubular fitting 45 which passes through a bore in sleeve member 33 and the housing 11 to provide a suction outlet for aspirating the inner elongated flexible tubular member 15. By making the motor drive shaft itself hollow, the stationary guidewire can be fed through the entire system. Flushing saline or other solution input is provided through a further access tube 46 which extends through an additional bore in the housing 11 which communicates with the chamber 37.

In operation, the elongated catheter assembly is appropriately introduced into the vascular system, as through the femoral artery, and advanced along the previously inserted guidewire 16, navigating through the vascular system to the appropriate arterial or other location of interest placing the cutter tip 17 adjacent to the atheroma or other lesion or blockage material to be excised from the vessel. The annular recessed diameter of the outer catheter member 12, at 19, aids in preventing clogging of the ports 20 during the insertion of the catheter through the arterial system. A flushing liquid such a saline is introduced through the fitting 46 into the chamber 37 of the housing 11 and flows through the lumen of the outer tubular member 12 outside the outer wall of the inner tubular member 15. The liquid then exits the radial ports 20 located radially about the side wall of the outer tubular member 12 near is distal end 13. Concurrently, a suitable source of suction or negative pressure is applied to the fitting 45 in a well-known matter to operate in conjunction with the flushing solution to aspirate the flushing liquid along with blood and/or tissue or other debris which may be excised from the atheroma or arterial blockage is drawn through the openings 24 in the cutter head 17 through the lumen of the inner tubular member into a suitable receptacle (not shown).

The motor 39 is energized to rotate the hollow manifold member of the rotary union within its tubular sleeve and thereby drive the tube 15 to rotate the cutter head 17 as desired. The catheter is advanced utilizing modest pressure between the cutter head 17 and the tissue to be excised so that the tissue is finely divided by the rapidly spinning cutter head and washed by blood and flushing liquid through the central lumen of the tube 15 and into a collecting receptacle (not shown). Once the atheroma has been completed penetrated, blood flow through the blood vessel is restored.

The position of the cutter head within the vessel can be adjusted with the necessary degree of precision during the procedure utilizing the guidewire to achieve complete removal of the blockage. In this manner, the attitude of the cutting head can be controlled and modulated with some leeway without the danger of inadvertent or unintentional damage to the vessel wall.

FIGS. 4 and 5 show an alternate embodiment of the atherectomy catheter of the invention in which an alternative guidewire 50 is provided in the nose of the cutter head 17 and which is fixed in a manner which allows it to rotate with the cutter head in a loosely fitted or journaled arrangement in which it is free to be held or free to turn with the cutter element 17 depending on the resistance to turning. This form of guidewire provides a certain amount of guidance for the catheter through the arterial system of interest without the necessity of having the guidewire extend throughout the entire length of the inner lumen at 15. Thus, the guidewire 50 may be rivetted to the opening 23 and the cutter member 17 in a manner which allows very little wobble of the guidewire but which allows it to rotate freely within the opening 23.

FIG. 6 illustrates yet another embodiment of the atherectomy catheter of the invention in which the annular spacer member 22 is not used and the cutter head or cutting tool 117 is in the shape of a full oval section and connected directly to the inner catheter 15. In addition, openings 20 may be replaced by annular space 120 or a combination of the holes 20 (shown in phantom) and annular spacer 120 used for the infusion of flushing liquid.

The present invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices and that various modifications, both as to equipment details and operating procedures, can be accomplished without departing from the scope of the invention itself.

What is claimed is:

1. A surgical cutting system for excising abnormal tissue deposits from the interior of a vascular passage or vessel of interest comprising:

(a) an outer hollow elongated flexible catheter tube having an outside diameter smaller than and capable of being advanced through the lumen of the vessel of interest, the outer tubular member having a proximal end and a distal end;

(b) an inner hollow elongated flexible catheter tube coaxially disposed within the outer tube and having a proximal end and a distal end with the outside of the inner catheter tube journalled for rotation inside the outer tube;

(c) drive means connected to the proximal end of the inner catheter tube for rotating the inner catheter tube;

(d) a substantially hollow symmetric, generally cylindrically symmetric cutting tool fixed to the distal end of the inner catheter tube member, having an oval-shaped distal nose portion of diminishing diameter and a tubular proximal portion, the nose portion further comprising a plurality of elongate radially disposed cutting openings extending along and rearward from a point near the center of the distal nose thereof, the openings being in communication with the hollow interior and disposed such that an edge thereof excises tissue encountered upon rotation of the cutting tool about its longitudinal axis, the excised tissue being directed into the hollow interior of the tool, wherein the location of plurality of openings is limited to the distal portion of diminishing diameter such that the cutting surfaces are precluded from engaging tissue at the full diameter of the cutting tool, the hollow interior of the cutting tool further being in communication with the interior of the inner tubular member;

(e) a central opening in the nose of the cutting tool; and (f) a guidewire of fixed longitudinal disposition having a proximal end journal mounted in the central opening in the nose of the cutting tool and a distal end protruding from the central opening substantially parallel to the longitudinal axis of the cutting tool, the journal mounting allowing the guidewire the freedom to rotate with the cutting tool or remain stationary.

2. A surgical cutting system for excising deposits from the interior of a blood vessel of interest comprising:

(a) an outer elongated flexible catheter tube having an outside diameter smaller than and capable of being advanced through the lumen of the vessel of interest, the outer catheter tube having a proximal end and a distal end, the distal end having an outside diameter which is necked down with respect to the diameter of the remaining portion of the outer catheter tube, and at least one radial opening for passing fluid therethrough near the distal end of the outer catheter tube;

(b) a rotatable inner elongated flexible catheter tube coaxially disposed for rotation within the outer tube and having a proximal end and a distal end, the outside diameter of the inner tube being of a size to be journalled for rotation in the necked-down portion of the outer catheter tube, the distal end of the inner tube extending a fixed distance out beyond the necked-down distal end of the outer catheter tube member;

(c) a substantially hollow cylindrically cutting tool having a symmetric, substantially oval-shaped distal nose having a narrowed frontal portion of diminishing diameter fixed to the distal end of the rotatable inner catheter tube member, the nose portion further comprising a plurality of radially disposed cutting openings extending along and rearward from a point near the center thereof, the openings being in communication with the hollow interior and disposed such that an edge thereof excises tissue upon rotation of the cutting tool about its longitudinal axis, the excised tissue being generally directed into the hollow interior of the tool, wherein the plurality of openings are elongated but do not extend beyond the narrowed frontal portion of the oval-shaped nose of diminishing diameter such that the tissue excised upon rotation of the cutting tool is less than the full diameter of the cutting tool, the hollow interior further being in communication with the interior of the inner catheter tubular member;

(d) a guidewire of fixed longitudinal disposition having a proximal end journal mounted in the central opening in the nose of the cutting tool and a distal end protruding from the central opening substantially parallel to the longitudinal axis of the cutting tool, the journal mounting allowing the guidewire the freedom to rotate with the cutting tool or remain stationary; and (e) drive means connected to the proximal end of the inner catheter tube for rotating the inner catheter tube member thereby rotating the cutter member to excise tissue deposits.

3. A surgical cutting system for excising deposits from the interior of a blood vessel of interest comprising:

(a) an outer elongated flexible tubular catheter member having an outside diameter smaller than the lumen of the vessel of interest and capable of being advanced through that lumen, the outer tubular member having a proximal end and a distal end and a continuous lumen therebetween;

(b) an inner elongated flexible tubular catheter member coaxially disposed within the outer tubular member and having a proximal end and a distal end, and describing a continuous lumen therebetween, the outside diameter of the inner tubular catheter member being of a size to allow the inner tubular member to be journalled in the outer catheter member;

(c) a substantially hollow cutting tool describing a symmetric, generally oval shape having a proximal end and a distal end, the proximal end being fixed to the distal end of the inner catheter member, the distal portion having an elliptical nose of a reduced and diminishing diameter having a plurality of radially disposed cutting openings near the center of the nose, the openings being in communication with the hollow interior and configured such that an edge thereof excises tissue encountered upon rotation of the cutting tool about its longitudinal axis, the excised tissue being directed into the hollow interior of the tool, wherein the plurality of openings are elongated but limited in location to the central region of the distal portion of reduced and diminishing diameter such that the cutting surfaces are precluded from engaging tissue adjacent the full diameter of the cutting tool, the hollow interior further being in communication with the interior of the inner catheter tubular member;

(d) drive means connected to the proximal end of the inner catheter tube for rotating the inner catheter tubular member thereby rotating the cutting tool member to excise tissue deposits;

(e) perfusion means for introducing a flushing liquid into the lumen of the outer catheter tube outside of the inner catheter tube;

(f) a distal opening in the outer catheter tube allowing the liquid to perfuse;

(g) aspiration means for aspirating liquids and excised debris through the openings in the cutting tool and the lumen of the inner catheter tube to a proximal exit opening; and (h) a guidewire of fixed longitudinal disposition having a proximal end journal mounted in the central opening in the nose of the cutting tool and a distal end protruding from the central opening substantially parallel to the longitudinal axis of the cutting tool, the journal mounting allowing the guidewire the freedom to rotate with the cutting tool or remain stationary.

4. A surgical cutting system for excising abnormal tissue deposits from the interior of a vascular passage or vessel of interest comprising:

(a) an outer hollow elongated flexible catheter tube having an outside diameter smaller than and capable of being advanced through the lumen of the vessel of interest, the outer tubular member having a proximal end and a distal end;

(b) an inner hollow elongated flexible catheter tube coaxially disposed within the outer tube and having a proximal end and a distal end with the outside of the inner catheter tube journalled for rotation inside the outer tube;

(c) drive means connected to the proximal end of the inner catheter tube for rotating the inner catheter tube;

(d) a substantially hollow symmetric, generally cylindrically symmetric cutting tool fixed to the distal end of the inner catheter tube member, having an oval-shaped distal nose portion of diminishing diameter and a tubular proximal portion, the nose portion further comprising a plurality of elongate radially disposed cutting openings extending along and rearward from a point near the center of the distal nose thereof, the openings being in communication with the hollow interior and disposed such that an edge thereof excises tissue encountered upon rotation of the cutting tool about its longitudinal axis, the excised tissue being directed into the hollow interior of the tool, wherein the plurality of openings are wholly contained in the distal portion of diminished diameter and spaced from any portion of undiminished diameter such that the cutting surfaces only engage in front of the cutting tool, the hollow interior of the cutting tool further being in communication with the interior of the inner tubular member; and (e) a non-rotating guidewire means having a proximal and a distal end and over which the system is threaded such that the guidewire is disposed in the inner catheter tube member and extends beyond both the proximal and distal ends thereof, the distal end of the guidewire means protruding from a central bore provided in the nose of the cutting tool, the inner tube member and the cutting tool being free to rotate about the guidewire means, the proximal end of the guidewire extending through the drive means on the proximal end to allow external control and operation of the guidewire independent of the operation of the remainder of the system.

5. The apparatus of claim 4 further comprising perfusion means for introducing a flushing liquid into the lumen of the outer tube outside of the inner tube and at least one radial fluid passage near the distal end of the outer tube for perfusing the liquid and aspiration means for aspirating liquids through the cutting tool openings via the lumen of the inner tube.

6. The surgical cutting system of claim 4 further comprising fluid outlet means for passing aspirated liquids and excised debris conducted from the excising openings in the cutting tool via the lumen of the inner catheter tube member to the proximal end thereof.

7. The apparatus of claim 4 further comprising:

at least one radial fluid passage opening formed at or near the distal end of the outer catheter tube;

infusion means associated with the drive means for introducing a flushing liquid between the inner and outer catheter tubes, the flushing liquid exiting the lumen of the outer catheter tube through the at least one radial fluid passage opening; and aspiration means for aspirating liquids and excised debris through the openings in the cutting tool, via the lumen of the inner catheter tube and out the proximal end of the inner catheter tube.

8. A surgical cutting system for excising deposits from the interior of a blood vessel of interest comprising:

(a) an outer elongated flexible catheter tube having an outside diameter smaller than and capable of being advanced through the lumen of the vessel of interest, the outer catheter tube having a proximal end and a distal end, the distal end having an outside diameter which is necked down with respect to the diameter of the remaining portion of the outer catheter tube, and at least one radial opening for passing fluid therethrough near the distal end of the outer catheter tube;

(b) a rotatable inner elongated flexible catheter tube coaxially disposed for rotation within the outer tube and having a proximal end and a distal end, the outside diameter of the inner tube being of a size to be journalled for rotation in the necked-down portion of the outer catheter tube, the distal end of the inner tube extending a fixed distance out beyond the necked-down distal end of the outer catheter tube member;

(c) a substantially hollow cylindrical cutting tool having a symmetric, substantially oval-shaped distal nose having a narrowed frontal portion of diminishing diameter fixed to the distal end of the rotatable inner catheter tube member, the nose portion further comprising a plurality of radially disposed cutting openings extending along and rearward from a point near the center thereof, the openings being in communication with the hollow interior and disposed such that an edge thereof excises tissue upon rotation of the cutting tool about its longitudinal axis, the excised tissue being generally directed into the hollow interior of the tool, wherein the plurality of openings are elongated but are entirely contained in the narrowed frontal portion of the oval,shaped nose of diminishing diameter and spaced from any portion of undiminished diameter such that the only tissue excised upon rotation of the cutting tool is in front of the cutting tool, the hollow interior further being in communication with the interior of the inner catheter tubular member;

(d) drive means connected to the proximal end of the inner catheter tube for rotating the inner catheter tube member thereby rotating the cutter member to excise tissue deposits; and (e) a non-rotating guidewire means having a proximal and a distal end and over which the system is threaded such that the guidewire is disposed in the inner catheter tube member and extends beyond both the proximal and distal ends thereof, the distal end of the guidewire means protruding from a central opening provided in the nose of the cutting tool, the inner tube member and the cutting tool being free to rotate around the guidewire means, the proximal end of the guidewire extending through the drive means on the proximal end to allow external control and operation of the guidewire independent of the operation of the remainder of the system.

9. The apparatus of claim 8 further comprising:

infusion means associated with the drive means for introducing a flushing liquid between the inner and outer catheter tubes, the flushing liquid exiting the lumen of the outer catheter tube through the at least one radial opening; and aspiration means for aspirating liquids and excised debris through the openings in the cutting tool, via the lumen of the inner catheter tube and out the proximal end of the inner catheter tube.

10. A surgical cutting system for excising deposits from the interior of a blood vessel of interest comprising:

(a) an outer elongated flexible tubular catheter member having an outside diameter smaller than the lumen of the vessel of interest and capable of being advanced through that lumen, the outer tubular member having a proximal end and a distal end and a continuous lumen therebetween;

(b) an inner elongated flexible tubular catheter member coaxially disposed within the outer tubular member and having a proximal end and a distal end, and describing a continuous lumen therebetween, the outside diameter of the inner tubular catheter member being of a size to allow the inner tubular member to be journalled in the outer catheter member;

(c) a substantially hollow cutting tool describing a symmetric, generally oval shape having a proximal end and a distal end, the proximal end being fixed to the distal end of the inner catheter member, the distal end having an elliptical nose of a reduced and diminishing diameter having a plurality of radially disposed cutting openings near the center of the nose, the openings being in communication with the hollow interior and configured such that an edge thereof excises tissue encountered upon rotation of the cutting tool about its longitudinal axis, the excised tissue being directed into the hollow interior of the tool, wherein the plurality of openings are elongated but limited in location to the central region of the distal portion of reduced and diminishing diameter and spaced from any portion of undiminished diameter such that the cutting surfaces engage only tissue adjacent the front of the cutting tool, the hollow interior further being in communication with the interior of the inner catheter tubular member;

(d) drive means connected to the proximal end of the inner catheter tube for rotating the inner catheter tubular member thereby rotating the cutting tool member to excise tissue deposits;

(e) perfusion means for introducing a flushing liquid into the lumen of the outer catheter tube outside of the inner catheter tube;

(f) a distal opening in the outer catheter tube allowing the liquid to perfuse;

(g) aspiration means for aspirating liquids and excised debris through the openings in the cutting tool and the lumen of the inner catheter tube to a proximal exit opening; and (h) a non-rotating guidewire means having a proximal and a distal end and over which the system is threaded such that the guidewire is disposed in the inner catheter tube member and extends beyond both the proximal and distal ends thereof, the distal end of the guidewire means protruding from a central opening provided in the nose of the cutting tool, the inner tube member and the cutting tool being free to rotate around the guidewire means, the proximal end of the guidewire extending through the drive means on the proximal end to allow external control and operation of the guidewire independent of the operation of the remainder of the system.

11. The surgical cutting system of claim 10 wherein the distal opening in the outer catheter comprises a fluid outlet passage between the inner and outer catheter tubes at the distal end of the outer catheter tube that allows the flushing liquid to exit the lumen of the outer catheter at the distal end thereof.

12. The surgical device of claim 10 wherein the distal opening in the outer catheter comprises at least one radial fluid passage in the wall of the catheter tube.

* * * * *